United States Patent
Ryu

(10) Patent No.: US 10,895,530 B2
(45) Date of Patent: Jan. 19, 2021

(54) SENSOR COMBINING DUST SENSOR AND GAS SENSOR

(71) Applicant: HITACHI-LG DATA STORAGE KOREA, INC., Seoul (KR)

(72) Inventor: Jaeyong Ryu, Seoul (KR)

(73) Assignee: HITACHI-LG DATA STORAGE KOREA, INC., Seoul (KR)

( * ) Notice: Subject to any disclaimer, the term of this patent is extended or adjusted under 35 U.S.C. 154(b) by 150 days.

(21) Appl. No.: 16/197,056

(22) Filed: Nov. 20, 2018

(65) Prior Publication Data

US 2019/0195792 A1 Jun. 27, 2019

(30) Foreign Application Priority Data

Dec. 22, 2017 (KR) .......................... 10-2017-0178230

(51) Int. Cl.
| | | |
|---|---|---|
| *G01N 21/53* | (2006.01) | |
| *G01N 21/94* | (2006.01) | |
| *G01N 33/00* | (2006.01) | |
| *G01N 21/3504* | (2014.01) | |
| *G01N 21/3518* | (2014.01) | |

(52) U.S. Cl.
CPC ......... *G01N 21/53* (2013.01); *G01N 21/3504* (2013.01); *G01N 21/3518* (2013.01); *G01N 21/94* (2013.01); *G01N 33/0062* (2013.01); *G01N 33/0073* (2013.01); *G01N 2201/0683* (2013.01)

(58) Field of Classification Search
CPC .......... G01N 21/94; G01N 2021/3509; G01N 21/3504; G01N 21/532; G01N 21/53–538; G01N 21/3518
See application file for complete search history.

(56) References Cited

U.S. PATENT DOCUMENTS

| | | | |
|---|---|---|---|
| 2013/0295835 A1* | 11/2013 | Fleischer | ................. F24F 11/30 454/256 |
| 2016/0274024 A1* | 9/2016 | Han | ........................ G01N 21/49 |
| 2017/0320005 A1* | 11/2017 | Vo | ........................ B01D 46/442 |

* cited by examiner

*Primary Examiner* — Rebecca C Bryant
(74) *Attorney, Agent, or Firm* — Birch, Stewart, Kolasch & Birch, LLP

(57) ABSTRACT

The present invention provides a sensor combining a dust sensor and a gas sensor, comprising a light emitting unit for emitting light, a first light receiving unit for receiving scattered light which is emitted by the light emitting unit and scattered by dust to detect dust concentration, a mirror for changing a path of the emitted light which the light emitting unit emits, and a second light receiving unit for receiving the emitted light the path of which is changed by the mirror to detect gas concentration. An inflow section for introducing air into a detection space inside the sensor is formed in a Y-shaped tube in which a first inlet and a second inlet meet. The inflow section comprises a switch which selects a path through which air flows into the detection space out of the first inlet and the second inlet.

8 Claims, 4 Drawing Sheets

Concentration b > Concentration a

SENSOR COMBINING DUST SENSOR AND GAS SENSOR

This application claims the benefit of priority under 35 U.S.C. § 119(a) to Korean Patent Application No. 10-2017-0178230 filed on Dec. 22, 2017, which is incorporated by reference herein in its entirety.

BACKGROUND

Field

The present invention relates to a sensor combining a dust sensor and a gas sensor.

Related Art

As the population increases and the number of vehicles increases, air pollution becomes worse. There is a growing interest in dust, and air purifier demand is also increasing. For active air cleaning, an air cleaner needs a dust sensor to measure the degree of air pollution, that is, dust concentration in air.

Volatile organic halogen compounds such as trihalomethane, trichlorethylene and tetrachlorethylene, and volatile organic compounds VOC such as benzene of aromatic compounds which are used for adhesive substances are widely discharged from newly built apartments, cause malodors, cause headaches and atopic dermatitis, and are classified as carcinogens. So, there is a growing demand for air purifiers capable of removing such volatile organic compounds using a photocatalyst synthesis material. In order for the air purifier to remove such volatile organic compounds or $CO_2$, it is advantageous to measure gas concentration using a gas sensor.

As a dust sensor, a photoelectric dust sensor is mainly used. FIG. 1 conceptually shows the principle of the photoelectric dust sensor sensing dust.

The dust sensor of the photoelectric type comprises an air inlet and an outlet in a housing, passes air flowing from the air inlet through an air passage, and discharges the air through the air outlet. The dust sensor emits light toward the air passage via a light emitting unit disposed in the air passage, collects the light radiated by the light emitting unit and then scattered by dusts included in the air via a light receiving unit disposed in the air passage, and measures the concentration of dust contained in the air by using an electric signal of the light receiving unit.

If there is little dust or smoke in the air passing through the air passage, almost all the light emitted from the light emitting unit reaches a light shielding region where the light receiving portion is not disposed, so the amount of light received by the light receiving unit becomes very small. On the other hand, if there is some dust or smoke in the air passing through the air passage, a part of the light radiated from the light emitting unit is reflected by the dust or smoke in the air passage and is incident on the light receiving unit, and the light receiving amount of the light receiving unit is increased.

Thus, it is possible to detect the presence/absence of dust or smoke passing through the air passage based on the fluctuation of the output signal of the light receiving element (or photo detector) included in the light receiving unit, and it is possible to detect the concentration of dust or smoke passing through the air passage based on the output level of the light receiving element.

On the other hand, photoelectrically operating gas sensors utilize the property of gas to absorb light. A light emitting unit emits light in the air passage, and a light receiving unit receives the light directly. The light receiving unit receives only a reduced amount of light by the amount of light absorbed by the component gas to be measured so that the amount of light received by the light receiving unit decreases when the gas is present in air and the amount of light received by the light receiving unit increases when the gas is small. The concentration of the gas may be calculated based on the magnitude of the signal output from the light receiving unit.

Since the dust sensor uses the light scattered by dust, the light emitted by the light emitting unit should not enter the light receiving unit. On the other hand, the gas sensor uses the light that is not absorbed by a target gas, the light emitted by the light emitting unit must directly enter the light receiving unit.

As described above, since the operation principle of the dust sensor and the gas sensor are different, there is a problem in that the dust sensor and the gas sensor must be separately used even in the case of using both the dust sensor and the gas sensor such as an air purifier or a vehicle air sensor.

SUMMARY

Accordingly, the present invention has been made in view of such circumstances, and it is an object of the present invention to implement a dust sensor and a gas sensor in one structure.

A sensor combining a dust sensor and a gas sensor according to an embodiment of the present invention may comprise: a light emitting unit for emitting light; a first light receiving unit for receiving scattered light which is emitted by the light emitting unit and scattered by dust to detect dust concentration; a mirror for changing a path of the emitted light which the light emitting unit emits; and a second light receiving unit for receiving the emitted light the path of which is changed by the mirror to detect gas concentration.

In an embodiment, the sensor may further comprise an inflow section for introducing air into a detection space inside the sensor, the inflow section being formed in a Y-shaped tube in which a first inlet and a second inlet meet.

In an embodiment, the inflow section may comprise a switch which is disposed at a position where the first inlet 41 and the second inlet 42 meet and selects a path through which air flows into the detection space out of the first inlet and the second inlet.

In an embodiment, an impactor for limiting a size of particles entering the detection space may be disposed at one or more of the first inlet and the second inlet.

In an embodiment, the mirror may be implemented by a polarization mirror.

In an embodiment, the sensor may further comprise a tube-shaped guide disposed between the mirror and the second light receiving unit, tube-shaped guide having a metal-plated surface.

In an embodiment, the light emitting unit, the first light receiving unit and the second light receiving unit may be disposed such that a first direction in which the light emitting unit emits light, a second direction which is perpendicular to a surface from which the first light receiving unit receives the scattered light, and a third direction which is perpendicular to a surface from which the second light receiving unit receives the emitted light are perpendicular to each other.

In an embodiment, the sensor may further comprise a fan for generating suction force to allow air to flow into the sensor.

In an embodiment, the fan may change a number of rotations of a motor according to a first mode for detecting the dust concentration or a second mode for detecting the gas concentration.

In an embodiment, a first mode for detecting the dust concentration and a second mode for detecting the gas concentration may be alternated.

By combining a gas sensor with a dust sensor implemented as separate sensors, the space occupied by the two sensors can be reduced and the price can be lowered.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION

Figure 1:
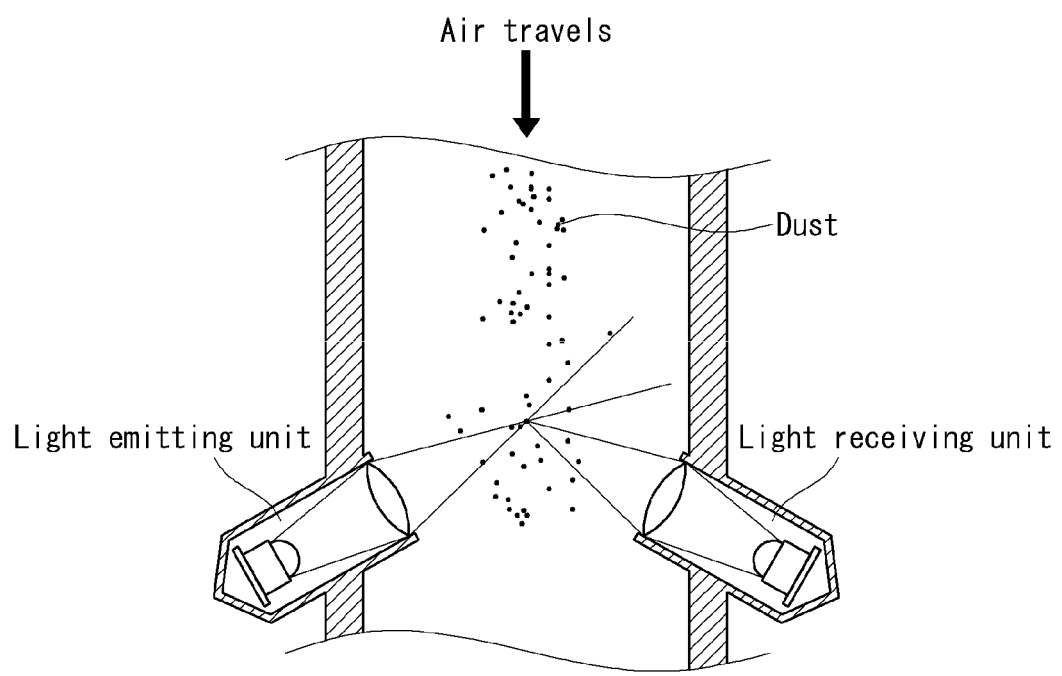
FIG. 1 conceptually shows the principle in which a photoelectric dust sensor senses a dust concentration.

Hereinafter, preferred embodiments of the present invention will be described in detail with reference to the accompanying drawings. Same reference numerals throughout the specification denote substantially identical components. In the following description, a detailed description of known functions and configurations incorporated herein will be omitted when it may make the subject matter of the present invention rather unclear.

The photoelectric type dust sensor is a device of measuring dust density by receiving the light scattered from fine particles such as dust contained in air via a light receiving element and outputting an electric signal.

The photoelectric type gas sensor is a device of measuring gas concentration by receiving the emitted light a portion of which has been absorbed by the gas contained in air so which is reduced in its quantity, and outputting an electrical signal.

The dust sensor detects a scattered light and the gas sensor detects a direct light. In order to combining the dust sensor and the gas sensor into one sensor, the present invention is characterized in that the light receiving unit for dust sensing is arranged perpendicular to a light path in the middle of the light path where the radiation light emitted from a light emitting unit travels to the light receiving unit for gas sensing, and a polarization mirror is disposed at a point passing the position where the light receiving unit for dust sensing is placed in the light path from the light emitting unit to the light receiving unit for gas sensing. The polarization mirror may prevent the light reflected from the surface of the light receiving unit for gas sensing from being reflected back to the light receiving unit for dust sensing.

Figure 2:
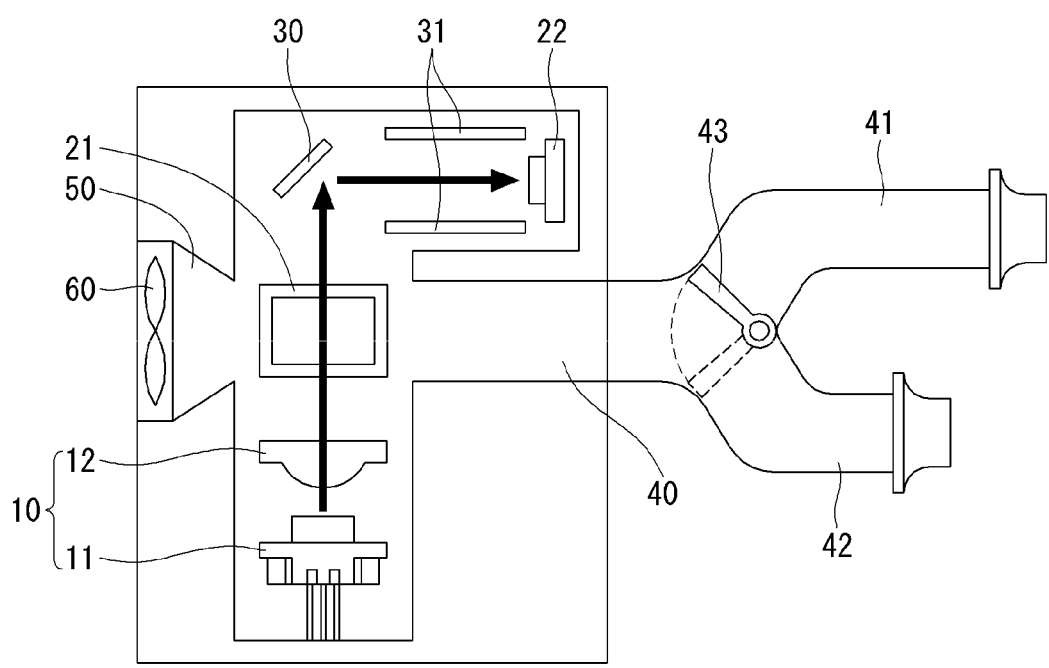
FIG. 2 illustrates a structure of a sensor incorporating a dust sensor and a gas sensor according to the present invention.

FIG. 2 illustrates a structure of a sensor incorporating a dust sensor and a gas sensor according to the present invention.

The sensor combining the dust sensor and the gas sensor according to the present invention may comprise a light emitting unit 10 for emitting radiation light in an air passage inside the sensor, a first light receiving unit 21 for collecting the light scattered by dust contained in the air flowing through the air passage, a second light receiving unit 22 for collecting the radiation light which has been emitted from the light emitting unit 10 and the amount of which is reduced because of the light absorption by the gas included in the air flowing along the air passage, and a polarization mirror 30 for changing the traveling path of the radiation light emitted by the light emitting unit 10.

The light emitting unit 10 and the first light receiving unit 21 are arranged at a right angle to each other, such that the first direction in which the light emitting unit 10 emits light and the second direction which is perpendicular to the surface from which the first light receiving unit 21 receives light are arranged perpendicular to each other. So, the radiation light emitted from the light emitting unit 10 does not directly enter the first light receiving unit 21. The first and second directions may be perpendicular to the direction along which the air entering the sensor travels, that is the direction of the air passage.

The light emitting unit 10 may comprise a light source 11 for radiating light of a predetermined band and a source lens 12 for converting the light radiated by the light source 11 into parallel light. The light source 11 may be a laser diode LD or a light emitting diode LED. The light source lens may be a collimating lens for converting divergent light into parallel light or a convex lens for converting parallel light into convergent light.

The first and second light receiving units 21 and 22 may comprise a light receiving element for generating an electric signal proportional to the amount of incident light, and may further comprise a receiving lens for condensing incident light on the light receiving element.

The inflow section 40 which is provided inside the sensor and through which air is injected into a detection space for detecting the concentration of dust or gas to form an air passage may include a first inlet 41 opened in a first mode for detecting dust concentration, a second inlet 42 opened in a second mode for detecting gas concentration, and a switch 43 for switching between the first mode and the second mode.

The combined sensor may further comprise a fan 60 for generating a suction force so that air can easily flow into the air passage through the inflow section 40 and flow out through an outflow section 50. The fan 60 may be omitted if air flows from the outside at a predetermined pressure.

The combined sensor may be further equipped with a guide 31 disposed between the polarization mirror 30 and the second receiving unit 22 so that the radiation light whose path is changed by the polarization mirror 30 is transmitted to the second light receiving unit 22 without loss. The guide 31 may be a rectangular or circular tube whose surface is metal-plated to serve as a waveguide.

The polarization mirror 30 changes the traveling path of the radiation light emitted by the light emitting unit 10, for example 90 degrees, such that of the radiation light entering the polarization mirror 30, only a first polarization component changes a polarization direction to become a second polarization component and proceeds to the second light receiving unit 22, and the second polarization component perpendicular to the first polarization component is absorbed by the polarization mirror 30 and does not advance to the second light receiving unit 22.

The reflected light reflected from the surface of the photo detector of the second light receiving unit 22 among the radiation light advancing to the second light receiving unit 22 is composed only of the second polarization component, is absorbed by the polarization mirror 30 and does not advance to the light emitting unit 10.

Thus, the polarization mirror 30 which is adopted to be disposed between the light emitting unit 10 and the second light receiving unit 22, may prevent the reflected light reflected by the second light receiving unit 22 from advancing to the light emitting unit 10 and from causing optical interference with the radiation light emitted from the light emitting unit 10. Also, the polarization mirror 30 may prevent scattered light from being further generated by the reflected light and flowing into the first light receiving unit 21.

The polarization mirror 30 may make the radiation light emitted by the light emitting unit 10 change the traveling direction by 90 degrees to advance to the second light receiving unit 22. The polarization mirror 30 may be mounted such that the radiation light advances in a third direction which is perpendicular both to the first direction in which the light emitting unit 10 emits light and the second direction which is perpendicular to the surface from which the photo detector of the first light receiving unit 21 receives scattered light. The second light receiving unit 22 may be mounted such that the surface of the photo detector of the second light receiving unit 22 is perpendicular to the third direction.

Figure 3:
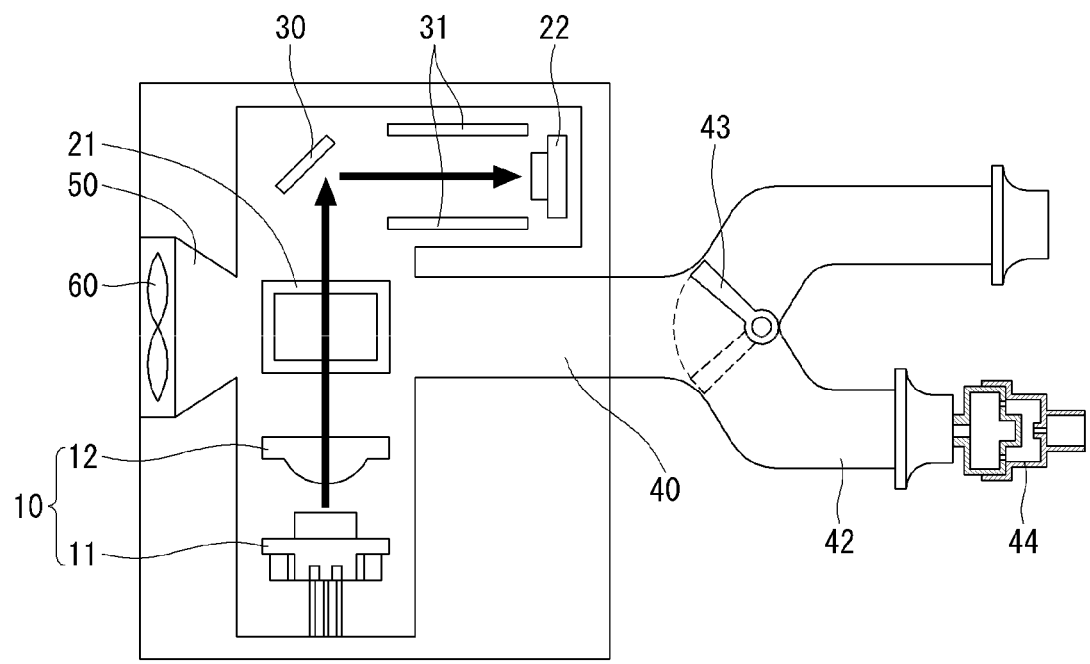
FIG. 3 shows an embodiment in which an impactor is mounted at an inlet through which gas is introduced in the combined structure of FIG. 2.

FIG. 3 shows an embodiment in which an impactor is mounted at an inlet through which gas is introduced in the combined structure of FIG. 2.

The inflow section 40 has a Y-shaped tube that combines two inlets to form one outlet. A first inlet 41 through which air containing dust is introduced and a second inlet through which air containing gas is introduced are combined to introduces air into a detection space for detecting dust concentration or gas concentration.

A switch 43 is disposed at a position where the first inlet 41 and the second inlet 42 meet. The switch 43 is rotated or moved according to a mode control signal so that only the first inlet 41 is connected to the outlet of the inflow section 40 or only the second inlet 42 is connected to the outlet of the inflow section 40. And the switch 43 may be implemented as a solenoid, for example.

The switch 43 blocks the second inlet 42 and connects the first inlet 41 to the outlet of the inflow section 40 in a first mode in which dust concentration is detected. And, the switch 43 blocks the first inlet 41 and connects the second inlet 42 to the outlet of the inflow section 40 in a second mode in which gas concentration is detected.

The pressure of the air inflow path needs to be different according to the first mode and the second mode. So, the second inlet 42 for detecting gas concentration is provided with an impactor 44 for limiting the size of particles introduced into the sensor, which prevents the large particles causing measurement errors from entering the detection space.

In order to measure fine dust concentration, the first inlet 41 may also be equipped with an impactor 44 for preventing entry of large particles The combined sensor may further comprise a connector (not shown) to connect to a controller for controlling the operations of the sensor. The combined sensor receives control signals for driving the light emitting unit 10, the first and second light receiving unit 21 and 22 and the fan 50 from the controller via the connector, and sends the output signals of the first and second light receiving unit 21 and 22 to the controller. The control signals may further include the mode control signal indicating the first mode or the second mode to select a mode.

The controller may output the mode control signal alternating between the first mode and the second mode in a time division manner so that the combined sensor can alternately output the output signals indicating the dust concentration and the gas concentration.

The fan 50 may vary the suction force according to the mode control signal, and may change the number of rotations of a motor according to the mode control signal.

Figure 4:
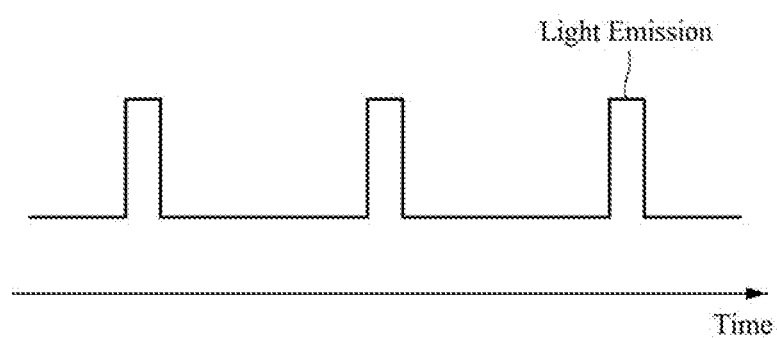
FIG. 4 shows optical pulses emitted from a light source of the sensor.
Figure 5:
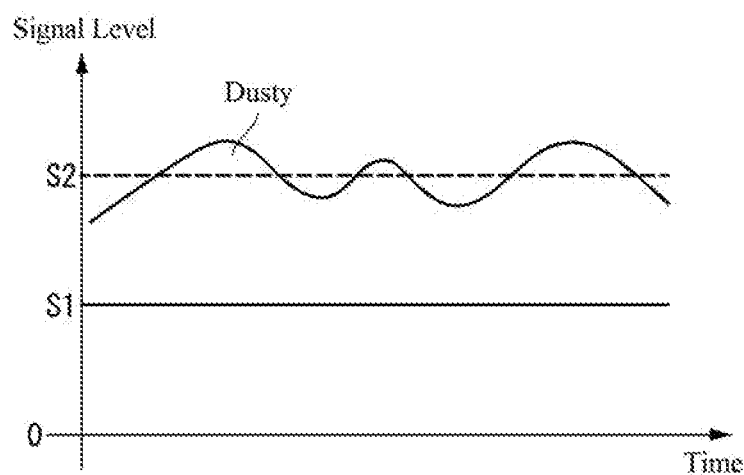
FIG. 5 shows a signal output from a first light receiving unit detecting dust concentration.
Figure 6:
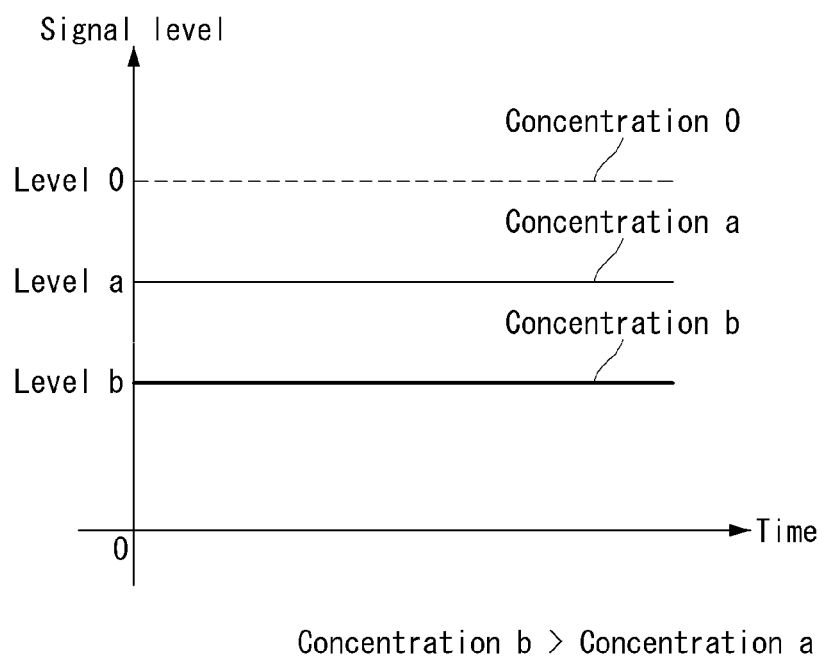
FIG. 6 shows a signal output from a second light receiving unit detecting gas concentration

The light emitting unit 10, as shown in FIG. 4, radiates light in a periodic pulse shape. As shown in FIG. 5, the first light receiving unit 21 for detecting dust concentration 21 converts the light incident on a photo detector into an electric signal and outputs the electric signal. As shown in FIG. 6, the second light receiving unit 22 for detecting gas concentration 21 converts the light incident on the photo detector into an electric signal and outputs the electric signal. In FIG. 6, it is assumed that the gas concentration is constant during the time that the output of the signal is displayed on the graph.

In the first mode measuring the dust concentration, even if there is no dust in the air passing through an air passage path, light radiated from the light emitting unit 10 is irregularly reflected inside the sensor and a small amount of light is received by the first light receiving unit 21. So, as shown in FIG. 5, the level of the output signal of the photo detector has a constant value SI even if there is no dust. The photo detector of the first light receiving unit 21 outputs a signal which changes in the form of a curve in FIG. 5 according to the concentration of dust contained in the air passing through the air passage path.

In the second mode measuring the gas concentration, when there is no target gas to be detected in the air passing through an air passage path, all of the radiation light emitted from the light emitting unit 10 enters the second light receiving unit 22, so the photo detector of the second light receiving unit 22 outputs the signal of "level 0" indicated by "concentration 0" in FIG. 6. When the target gas to be detected is included in the air passing through an air passage path, some of the radiation light emitted from the light emitting unit 10 is absorbed by the target gas and the remaining of the radiation light enters the second light receiving unit 22, so the output level of the photo detector is lowered. The higher the concentration of the target gas is, the more the output level is lowered. As shown in FIG. 6, when "concentration b" is higher than "concentration a", "level b" which is the output level of "concentration b" becomes lower than "level a" which is the output level of "concentration a".

Throughout the description, it should be understood by those skilled in the art that various changes and modifications are possible without departing from the technical principles of the present invention. Therefore, the technical scope of the present invention is not limited to the detailed descriptions in this specification but should be defined by the scope of the appended claims.

What is claimed is:

1. A sensor combining a dust sensor and a gas sensor, comprising:
   a light emitting unit for emitting light;
   a first light receiving unit for receiving scattered light which is emitted by the light emitting unit and scattered by dust to detect dust concentration;
   a mirror for changing a path of the emitted light which the light emitting unit emits;
   a second light receiving unit for receiving the emitted light the path of which is changed by the mirror to detect gas concentration; and
   a fan for generating suction force to allow air to flow into the sensor,
   wherein the fan changes a number of rotations of a motor according to a first mode for detecting the dust concentration or a second mode for detecting the gas concentration.

2. The sensor of claim 1, further comprising:
   an inflow section for introducing air into a detection space inside the sensor, the inflow section being formed in a Y-shaped tube in which a first inlet and a second inlet meet.

3. The sensor of claim 2, wherein the inflow section comprises a switch which is disposed at a position where the first inlet and the second inlet meet and selects a path through which air flows into the detection space out of the first inlet and the second inlet.

4. The sensor of claim 2, wherein an impactor filter for limiting a size of particles entering the detection space is disposed at one or more of the first inlet and the second inlet.

5. The sensor of claim 1, wherein the mirror is implemented by a polarization mirror.

6. The sensor of claim 1, further comprising:
   a tube-shaped guide disposed between the mirror and the second light receiving unit, tube-shaped guide having a metal-plated surface.

7. The sensor of claim 1, wherein the light emitting unit, the first light receiving unit and the second light receiving unit are disposed such that a first direction in which the light emitting unit emits light, a second direction which is perpendicular to a surface from which the first light receiving unit receives the scattered light and a third direction which is perpendicular to a surface from which the second light receiving unit receives the emitted light are perpendicular to each other.

8. The sensor of claim 1, wherein the first mode for detecting the dust concentration and the second mode for detecting the gas concentration are alternated.

* * * * *